United States Patent [19]

Raines et al.

[11] Patent Number: 5,037,390
[45] Date of Patent: Aug. 6, 1991

[54] SYSTEM AND METHOD FOR MIXING PARENTERAL NUTRITION SOLUTIONS

[76] Inventors: Kenneth Raines, 1760 Easthill Dr.; Gary Horner, 3098 Glendon Rd., both of Bethlehem, Pa. 18017

[21] Appl. No.: 458,418

[22] Filed: Dec. 28, 1989

[51] Int. Cl.$^5$ .............................................. A61M 37/00
[52] U.S. Cl. ...................................... 604/83; 604/88; 604/246; 604/411; 211/74
[58] Field of Search .................... 604/407, 411, 80–86, 604/246, 248; 248/311.2, 311.3; 211/204, 74

[56] References Cited

U.S. PATENT DOCUMENTS

| | | | |
|---|---|---|---|
| 2,254,994 | 9/1941 | Buttand | 604/83 X |
| 3,552,577 | 1/1971 | Latham, Jr. | 248/311.3 X |
| 3,861,388 | 1/1975 | Vaughn | 604/86 |
| 4,253,501 | 3/1981 | Ogle | 141/27 |
| 4,447,236 | 5/1984 | Quinn | 604/169 |
| 4,729,401 | 3/1988 | Raines | 137/512 |
| 4,787,898 | 11/1988 | Raines | 604/411 |
| 4,915,688 | 4/1990 | Bischof et al. | 604/83 |

Primary Examiner—John D. Yasko
Assistant Examiner—Adam J. Cermak
Attorney, Agent, or Firm—Shoemaker and Mattare, Ltd.

[57] ABSTRACT

An apparatus and method for mixing parenteral nutrition solutions from additives in a plurality of vials containing the additives, in which a vented spike is inserted through a disposable rack and into the stoppered end of each vial, with the vials secured on the rack. The rack is engaged on a stand through a quick release fitting, and maintains the vials in a vertical orientation with the labels clearly visible. A dedicated syringe is connected with each vial in aligned relationship therewith through a unique two-way valve which is mounted to a manifold. In one form of the invention, the valve is attached directly on the manifold to reduce dead space volume and consequently reduce residual fluid in the system between purges. A flushing system is attached to one end of the manifold to flush any residual fluids into the final container at the end of a transfer process. The other end of the manifold may be attached in tandem with a further manifold in a further apparatus containing additional vials for admixing even further additives.

4 Claims, 7 Drawing Sheets

SYSTEM AND METHOD FOR MIXING PARENTERAL NUTRITION SOLUTIONS

FIELD OF THE INVENTION

This invention relates to the medical arts, and more particularly, to an apparatus and method for mixing parenteral nutrition solutions.

DESCRIPTION OF THE PRIOR ART

Parenteral nutrition typically involves the infusion into a patient of diverse active ingredients usually including pharmaceutically-active chemicals. These substances often cannot be pre-mixed, packaged, sterilized, prepared or stored together, however, for medical as well as practical reasons, their administration as mixtures is often preferred. Accordingly, the concept of parenteral nutrition has evolved into a process in which a complex mixture of pharmaceutically-active substances is made for administration to a patient. These mixtures generally include multiple base solutions to which are added numerous additives, sometimes as many as twelve or more. Once mixed, these parenteral materials are drawn from individual vials, capped with rubber stoppers, and with capacities ranging in size from 5 ml to 100 ml. Generally, different patients require different combinations of additives in varying concentrations, with each mixture adapted and customized to meet the needs of a particular patient and supplement the body's nutritional needs indicated by various diagnostic and blood chemistry tests routinely performed.

In a typical prior art method of parenteral nutrition, a basic parenteral nutrition solution of amino acid and 50% dextrose is prepared by trained personnel. Sterile, sealed, rubber-stoppered vials containing the various additives are assembled and placed under a laminar flow hood to produce a sterile environment. The sterility cap is removed from each vial and an empty sterile syringe is placed in front of each vial. Usually a pharmacist, knowing the drug additive order, picks up each vial, one at a time, verifies the contents, swabs the rubber stopper with alcohol, inserts the syringe needle, inverts the bottle and withdraws the desired amount of the additive. The needle is then withdrawn and the vial set down and moved toward the final parenteral administration container, where the site of injection on the bag or bottle is cleaned with alcohol and the needle inserted into the final container to insert the additive. Extreme care must be maintained not to puncture the side of the injection port of the bag during insertion and withdrawal of the needle.

This process is repeated numerous times daily for each solution admixture bag or bottle, sometimes as much as 12 times, three times a day for each 1000 ml container per patient. A medium to large size health facility or hospital may have as many as from 25 to 50 patients on total parenteral nutrition solutions on any given day. Thus, the technician or pharmacist may be required to prepare 75 to 150 parenteral nutrition solutions per day, involving manipulations for 900 to 1800 individual vials.

The number of manipulations and process steps required in the prior art process described above is extremely costly, time consuming and tedious, and increases the risk of danger in a breach in the sterile technique. Moreover, errors arising from inaccurate dosing from each vial is a serious problem. Further, there is increased danger of introducing cored rubber particles from the syringe punctures into the final container. In addition, non-vented vials can spread aerosolized drug or chemicals onto the preparer's hands during the multiple insertions required to prepare the final mixture. Significant cost is also incurred because of the continuous disposal of syringes and needles used in the transfer process.

In an effort to reduce or eliminate the foregoing problems, various closed systems and electronically controlled apparatus have been devised. One example of a closed system is described in U.S. Pat. No. 4,433,974, wherein a plurality of additives in individual containers are withdrawn using a syringe and then injected utilizing a multiple transfer valve into a container for the final mixture. This final container is then connected to a perfusion pump for infusion of the mixture into the patient. This system, while overcoming many of the problems mentioned above, requires manual manipulation of tubing clamps for each additive container, and cross-contamination can result from any residual fluid left in the conduits below the clamps. Moreover, the use of a single syringe to withdraw the materials from the various additive containers does not provide a ready visual reference for the sequence of mixing the additives, and/or the quantity of each additive withdrawn.

Accordingly, there is a need for an apparatus which is economical and easy to use in the mixing of parenteral nutrition solutions, which reduces or eliminates multiple manipulations of apparatus such as clamps or vials, aids in maintaining a sterile environment, provides a ready visual indication of the additive and the quantity of the additive being withdrawn, and minimizes the danger of introducing cored rubber particles into the parenteral solution.

SUMMARY OF THE INVENTION

It is therefore an object of the present invention to provide an apparatus that is economical and easy to use for mixing parenteral nutrition solutions.

Another object of the invention is to provide a closed system for the mixing of parenteral nutrition solutions, wherein the system affords a ready visual indication of the additive and the quantity of that additive being withdrawn from each additive container.

Yet another object of the invention is to provide an apparatus for mixing parenteral nutrition solutions, wherein a minimum number of manual manipulations are required to mix the additives.

A further object of the invention is to provide a parenteral nutrition admixture apparatus, in which containers of additives to be admixed are held on a disposable rack in aligned relationship with syringes for withdrawing additive from the containers, thereby providing visual reference of the additive selected and the quantity of that additive remaining.

Another object of the invention is to provide an apparatus for mixing parenteral nutrition solutions, in which unique valving means is associated with the vials containing the additives and with the remainder of the system so that minimal residual fluid is left in the system.

Yet another object of the invention is to provide a closed system for mixing parenteral nutrition solutions, with a flush connection for flushing any residual fluid from the system.

An even further object of the invention is to provide a fast and efficient method for mixing parenteral nutrition additives by eliminating all vial and syringe needle manipulations in the transfer process.

Another object of the invention is to provide an apparatus for use in the preparation of parenteral nutrition solutions, wherein the entire system is compact and designed to enhance sterile laminar air flow.

These and other objects and advantages of the invention are accomplished by an apparatus and method in which a vented spike is inserted through a disposable rack and into the stoppered end of each vial, with the vials secured on the rack. The rack is engaged on a stand through a quick release fitting, and maintains the vials in a vertical orientation with the labels clearly visible. A dedicated syringe is connected with each vial in aligned relationship therewith through a unique two-way valve which is mounted to a manifold. In one form of the invention, the valve is attached directly on the manifold to reduce dead space volume and consequently reduce residual fluid in the system between purges. A flushing system is attached to one end of the manifold to flush any residual fluids into the final container at the end of a transfer process. The other end of the manifold may be attached in tandem with a further manifold in a further apparatus containing additional vials for admixing even further additives.

BRIEF DESCRIPTION OF THE DRAWINGS

The foregoing as well as other objects and advantages of the invention will become apparent from the following detailed description when considered in conjunction with the accompanying drawings, in which like reference characters designate like parts throughout the several views, and wherein.

DETAILED DESCRIPTION OF THE PREFERRED EMBODIMENTS

Figure 1:
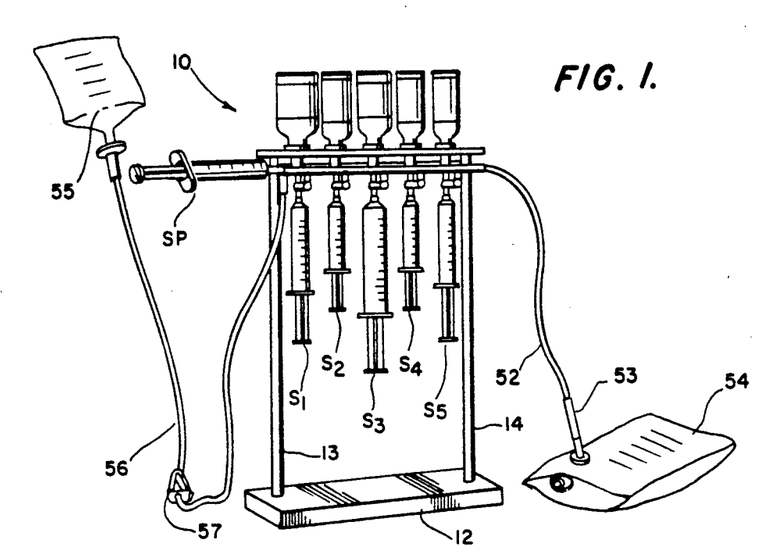
FIG. 1 is a perspective view of a first form of apparatus according to the invention.
Figure 2:
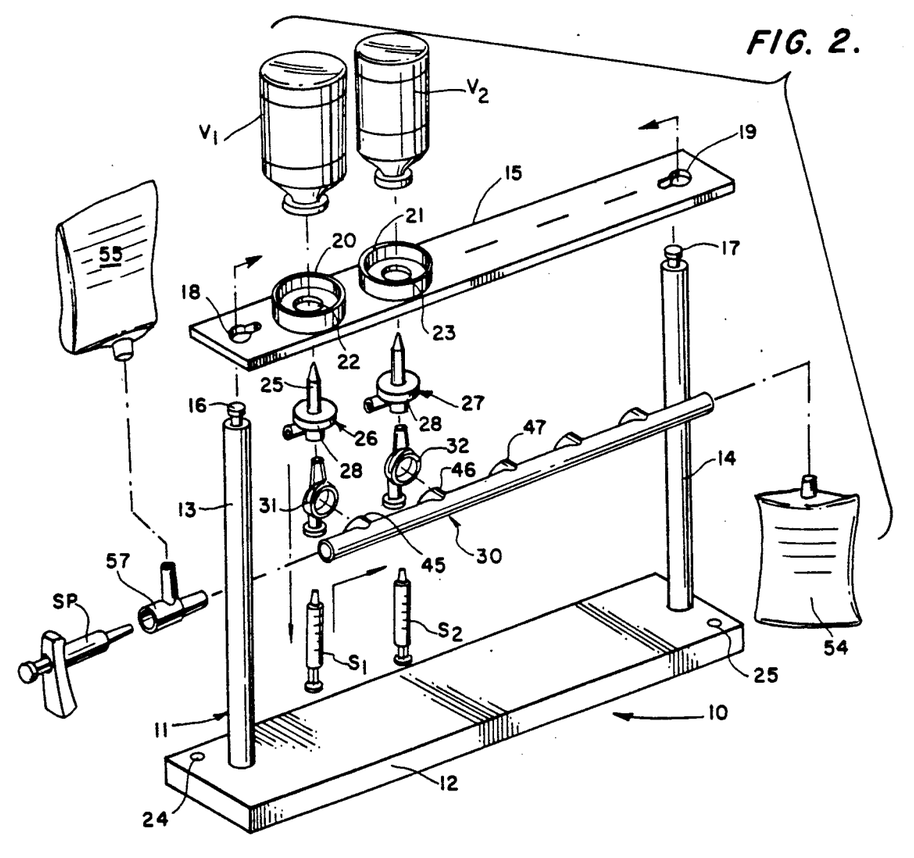
FIG. 2 is an exploded perspective view, with portions removed for purposes of clarity, of the apparatus of FIG. 1.
Figure 3:
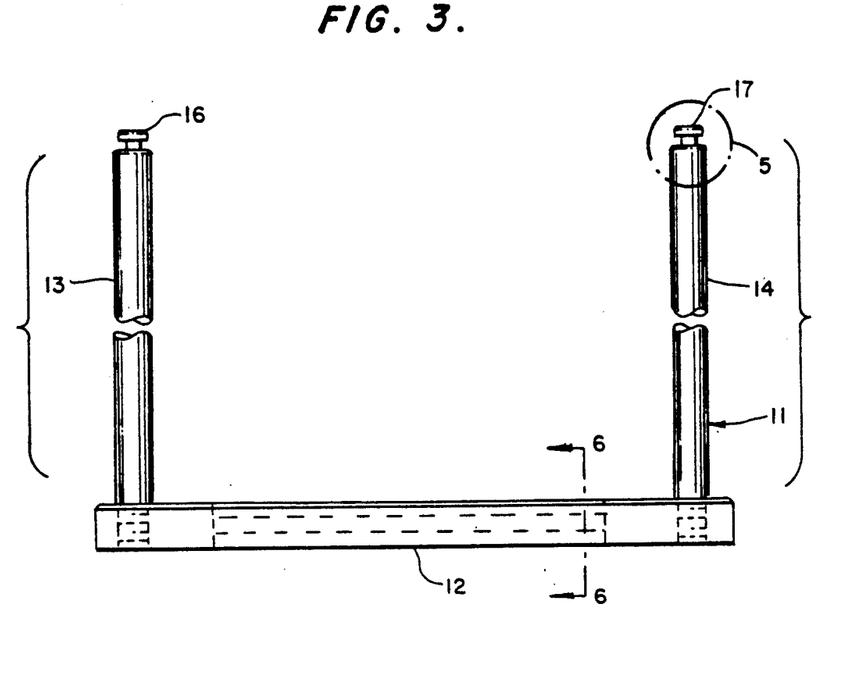
FIG. 3 is a side view in elevation, with portions broken away, of the stand for use with the rack that holds the vials in the apparatus of the invention.
Figure 4:
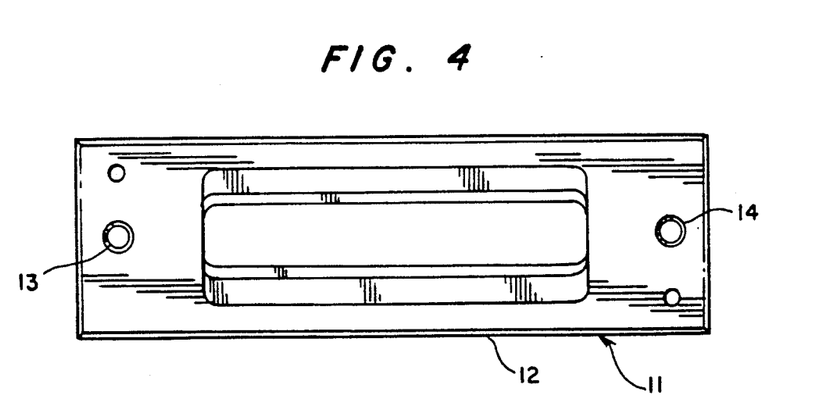
FIG. 4 is a top plan view of the stand of FIG. 3.
Figure 5:
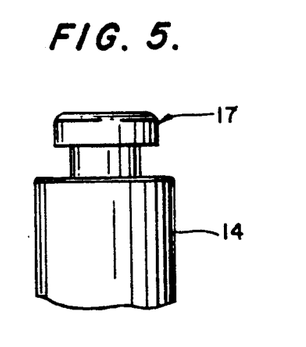
FIG. 5 is an enlarged fragmentary view in elevation of the portion of FIG. 3 circled at 5.
Figure 6:
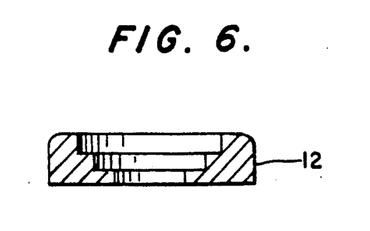
FIG. 6 is a transverse sectional view taken along line 6—6 in FIG. 3.
Figure 7:
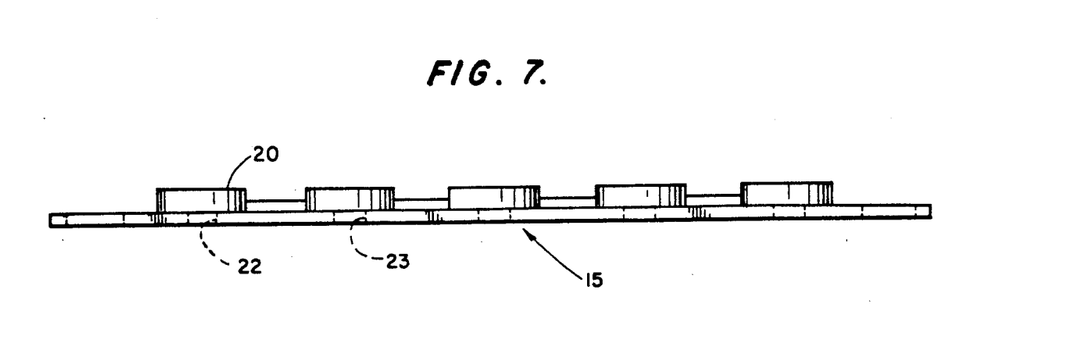
FIG. 7 is a side view in elevation of the disposable rack that is used to hold the vials in the apparatus of the invention and which is releasably attached to the stand of FIG. 3.
Figure 8:
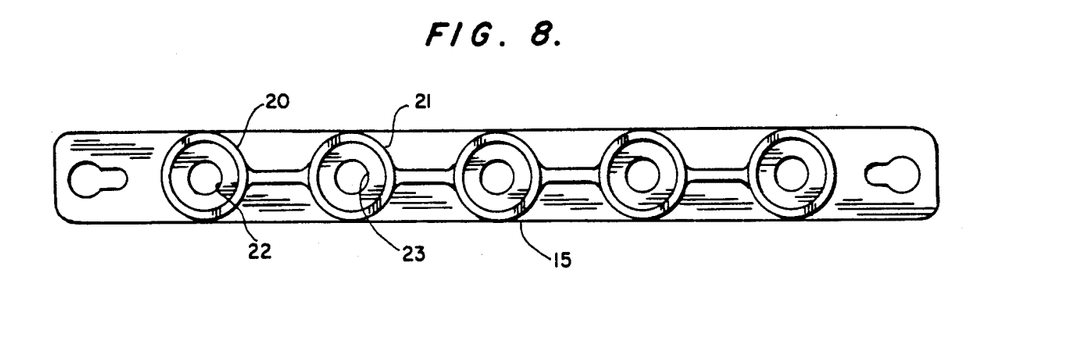
FIG. 8 is a top plan view of the rack of FIG. 7.

Referring more particularly to the drawings, a first form of apparatus in accordance with the invention is indicated generally at 10 in FIGS. 1 and 2.

The apparatus includes a novel stand 11 having a base plate 12 and upstanding arms 13 and 14 at its opposite ends. A disposable rack 15 is adapted to be releasably engaged with the upper ends of the arms 13 and 14 by means of headed projections 16 and 17 on the upper ends of the arms which engage in key hole slots 18 and 19 at the opposite ends of the rack 15. In this connection, the arms 13 and 14 have a normal, upright position with the headed ends engaged in the smaller section of the slots 18 and 19, to prevent withdrawal of the headed ends through the slots. The arms may be flexed outwardly relative to the rack 15 to align the headed ends 16 and 17 with the larger openings in the slots for removal and/or replacement of the rack on the stand. The rack includes a plurality of upstanding cylindrical walls or cup-shaped formations 20, 21, etc. with concentrically disposed openings 22, 23, etc. extending through the rack 15.

In a preferred construction, the rack 15 may comprise a plastic material such as rigid PVC, while the arms 13 and 14 may be made of stainless steel or the like. The stand may be secured to a support surface by any suitable means, such as fasteners (not shown) extended through openings 24 in the base plate 12.

Figure 9:
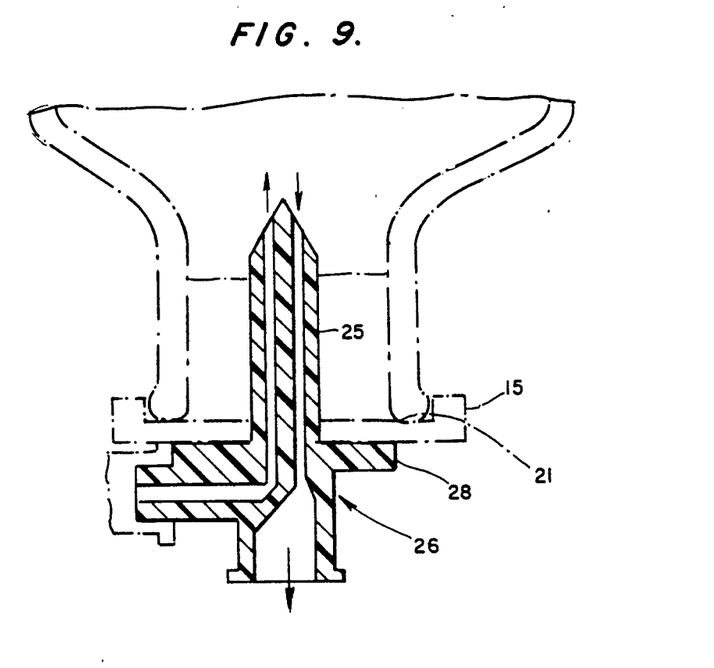
FIG. 9 is a greatly enlarged longitudinal sectional view of the vented spike used for piercing the stoppered ends of the vials.

A plurality of vented spikes 26, 27, etc., corresponding to the number of vials $V_1$, $V_2$, etc., each has a piercing end 25 which is inserted upwardly through a respective opening 22, 23, etc., and into the stoppered end of an associated vial placed in the cup-shaped formations 20, 21, etc, on top of the rack 15. A flange 28 on the vented spike engages beneath the rack 15 whereby the vials and vented spike are securely attached to the rack on opposite sides thereof. When the rack is assembled to the stand as shown in FIGS. 1 and 2, the vials are accordingly held in an upright position.

A manifold/valve assembly 30 is secured to the plurality of vented spikes 26, 27, etc., and includes a plurality of multi-way valves 31, 32, etc., with each valve being attached to a respective vented spike 26, 27, etc. As seen best in FIG. 10 through 13, each valve 31, 32, etc., comprises a valve body 33 having a tapered male end 34 on one end thereof for attachment to a respective vented spike 26, 27, etc., and a female tapered end 35 on the other end for attachment of a syringe $S_1$, $S_2$, etc.

Figures 10, 11, 12:
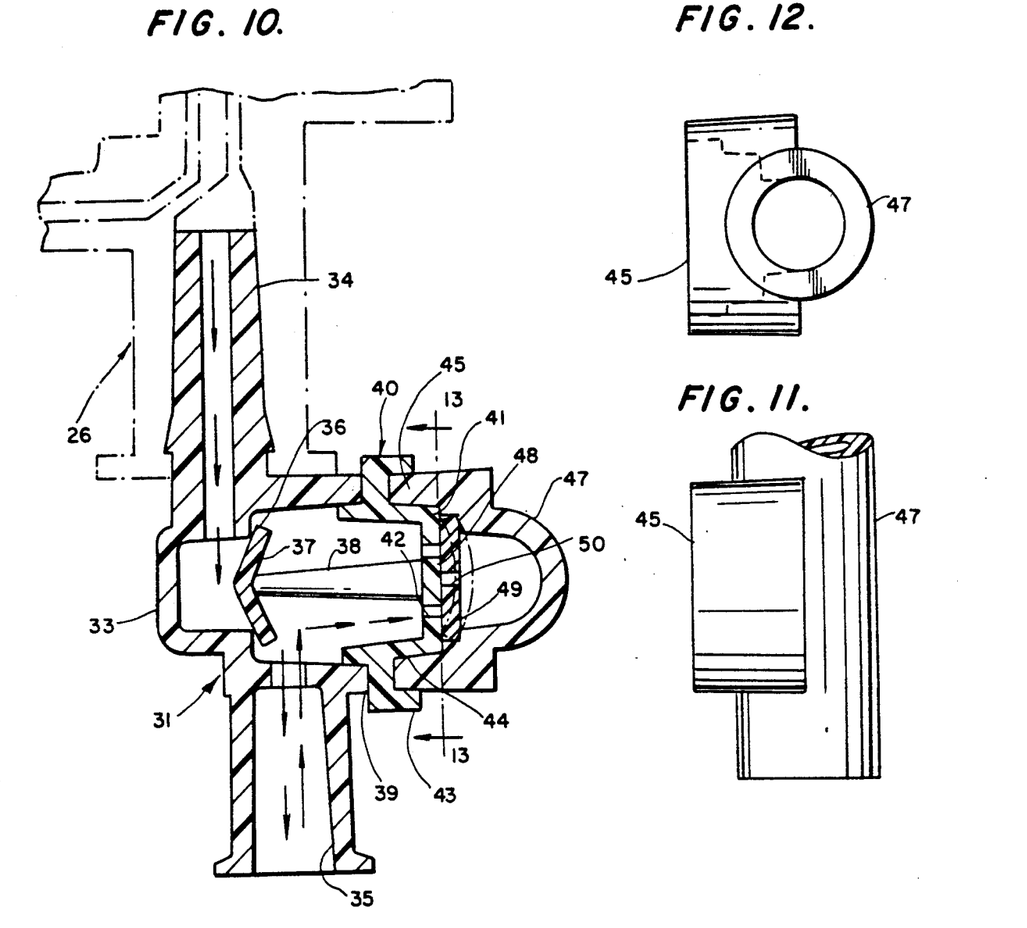
FIG. 10 is a greatly enlarged longitudinal sectional view of the unique multi-way valve used to connect the vials to the manifold.
FIG. 11 is an enlarged fragmentary top plan view of a portion of the manifold and a point of attachment to the valve of FIG. 10.
FIG. 12 is an end view of the manifold and attachment of FIG. 11.

The ends of the valve body are offset as seen best in FIG. 10, and a first valve seat 36 is defined therebetween for cooperation with a first check valve 37. The check valve 37 comprises a flexible disc normally held in closed position against the valve seat 36 by an elongate arm or stop 38.

The side 39 of the valve body opposite the seat 36 is open and a valve seat member 40 is secured thereon by any suitable means such as a sonic weld or the like. The seat member 40 includes an end wall 41 with a plurality of openings 42 formed therethrough. An annular flange or wall 43 defines an annular pocket 44 for receipt of a respective cylindrical projection 45, 46, etc. on the manifold 47. The seat member 40 is secured to the manifold by any suitable means such as a sonic weld or the like, whereby the valves 31, 32, etc. form an integral structure with the manifold 47. With the vented spikes and vials attached to the rack 15 as described above and with the manifold/valve assembly attached to the vented spikes, the apparatus results in a structure wherein each vial is held in aligned relationship with the respective valve and syringe $S_1$, $S_2$, etc., so that ready visual reference can be made to the additive which is being withdrawn at a particular time and to the quantity of that additive being withdrawn.

Figure 13:
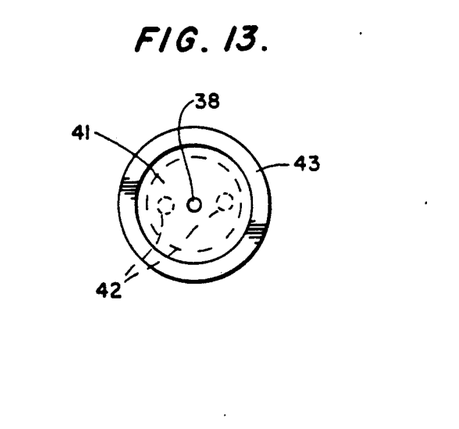
FIG. 13 is a view in section taken along line 13—13 of FIG. 10.
Figure 14:
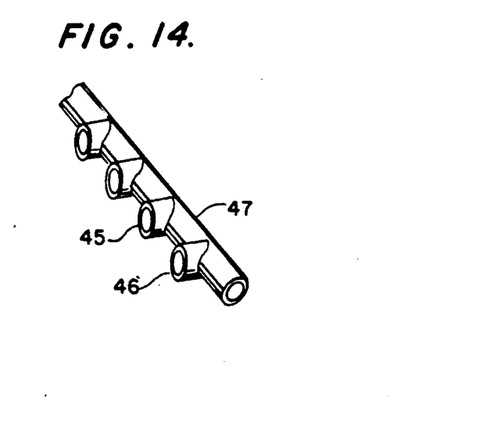
FIG. 14 is a fragmentary perspective view of the manifold and points of attachment for the valves.

As seen best in FIGS. 10, 12 and 13, the end wall 41 of seat member 40 defines a second valve seat 48 for cooperation with a normally closed flexible valving disc 49 that is secured at its periphery between the manifold 47 and the end wall 41 and has a central opening 50 therethrough so that when fluid pressure deforms the valving disc 49 away from the seat 48, flow can occur through the openings 42 in end wall 41 and through the opening 50 into the manifold 47. The valve disc 49 is shown in closed position in full lines in FIG. 10 and in open position in dot and dash lines.

In use of the apparatus, a plurality of vials $V_1$, $V_2$, etc., are assembled with a rack 15 and vented spikes 26, 27, etc., attached thereto as described previously. The rack is then engaged on the arms 13 and 14 of the stand 11, and the manifold/valve assembly 30 is attached to the vented spikes. Syringes $S_1$, $S_2$, are attached to the valves 31, 32, on the manifold/valve assembly, with the number of syringes corresponding to the number of vials and each syringe being dedicated to a specific vial and held in vertically aligned relationship thereto.

The respective syringes $S_1$, $S_2$, etc. are manipulated in a desired sequence to draw material from the respective vials $V_1$, $V_2$, etc. through the respective multi-way valves 31, 32, etc. and past valve disc 36 into the respective syringe. The syringe is then manipulated in a reverse direction to expel the previously withdrawn material back through the valve 31, 32, etc. and past the valve disc 49 into the manifold 47. From the manifold the material flows through a length of tubing 52, through a syringe 53 and into a final container 54 for the parenteral nutrition solution to be administered to a patient. The syringes are manipulated in turn as described above to withdraw desired additives from the respective vials through the valves, into the respective syringe and thence back through the associated valve into the manifold and to the container 54.

A container 55 is connected through a length of tubing 56 with a valved fitting 57 connected to the end of the manifold remote from the final container 54 and a syringe pump SP is connected with the conduit to draw a flushing solution, such as normal saline or the like, from the container 55 and force it through the manifold to remove any residual additives left therein following the transfer operation previously described. A suitable clamp 57 is positioned in the length of tubing 56 to interrupt flow therethrough as desired.

Figure 15:
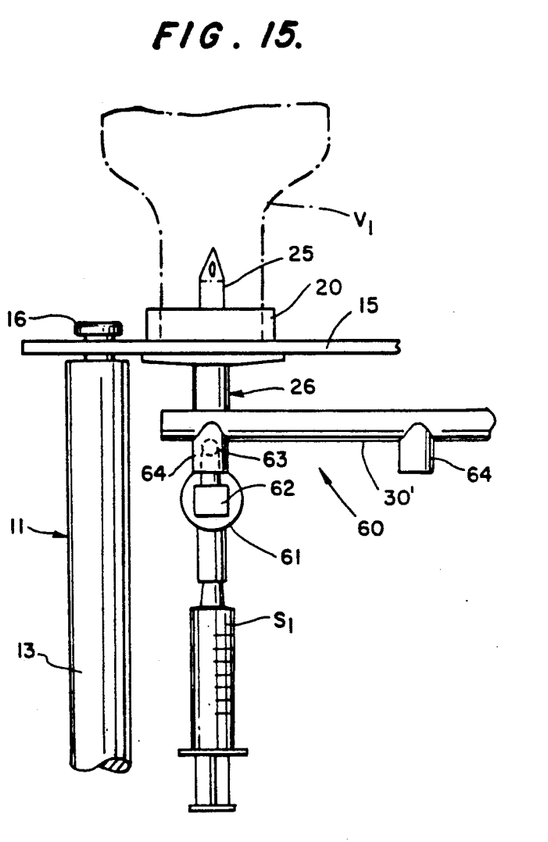
FIG. 15 is an enlarged fragmentary view in front elevation of a modified form of the invention wherein the rack and stand of FIG. 1 are used in combination with a modified valve and manifold.
Figure 16:
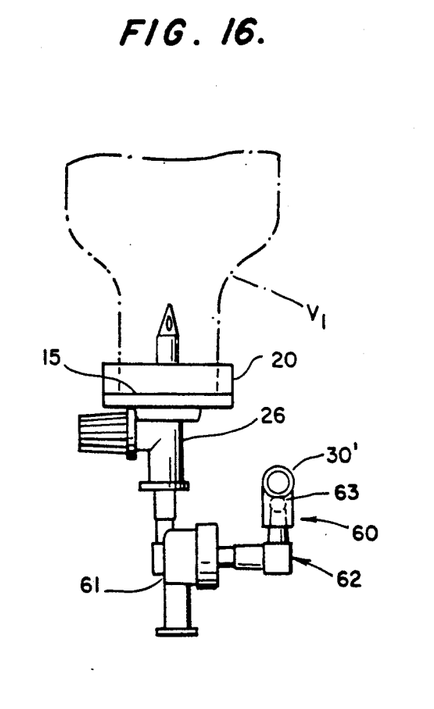
FIG. 16 is a fragmentary end view of the apparatus of FIG. 15.
Figure 17:
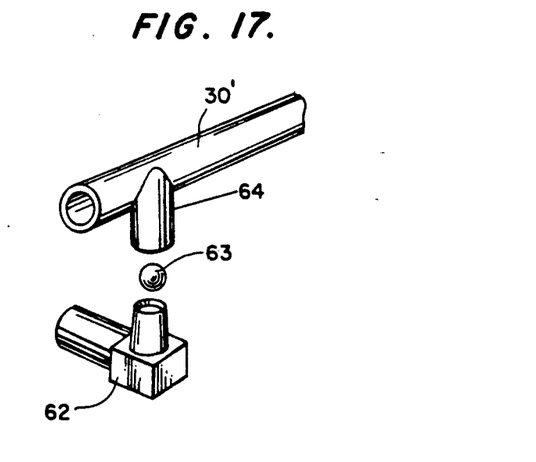
FIG. 17 is an exploded fragmentary perspective view of a portion of the manifold and the valved elbow connector for attaching the manifold to the valve in the apparatus of FIG. 15.

A first modification of the invention is indicated generally at 60 in FIGS. 15 through 17. In this form of the invention, a vented spike 26 connects with a vial $V_1$ through the disposable rack 15, which is supported on the stand 11 as previously described. In this form of the invention, however, a different multi-way valve 61 is used to connect the vented spike 26 to manifold 30'. The multi-way valve 61 used in this form of the invention is of the type shown and described in applicant's prior patent No. 4,729,401, and includes a pair of normally closed flexible discs positioned to control flow from the vial into a syringe $S_1$, and then from the syringe back through the valve and through an elbow fitting 62 into the manifold 30'. A check ball valve 63 is positioned in the elbow fitting for preventing reverse flow from the manifold 30' and avoiding cross contamination. The elbow fitting 62 is attached to the manifold 30' via a female coupling 64 formed integrally with the manifold. Except for the modified valve 61 and elbow fitting 62, this form of the invention is substantially the same as that previously described and functions in essentially the same way.

Figure 18:
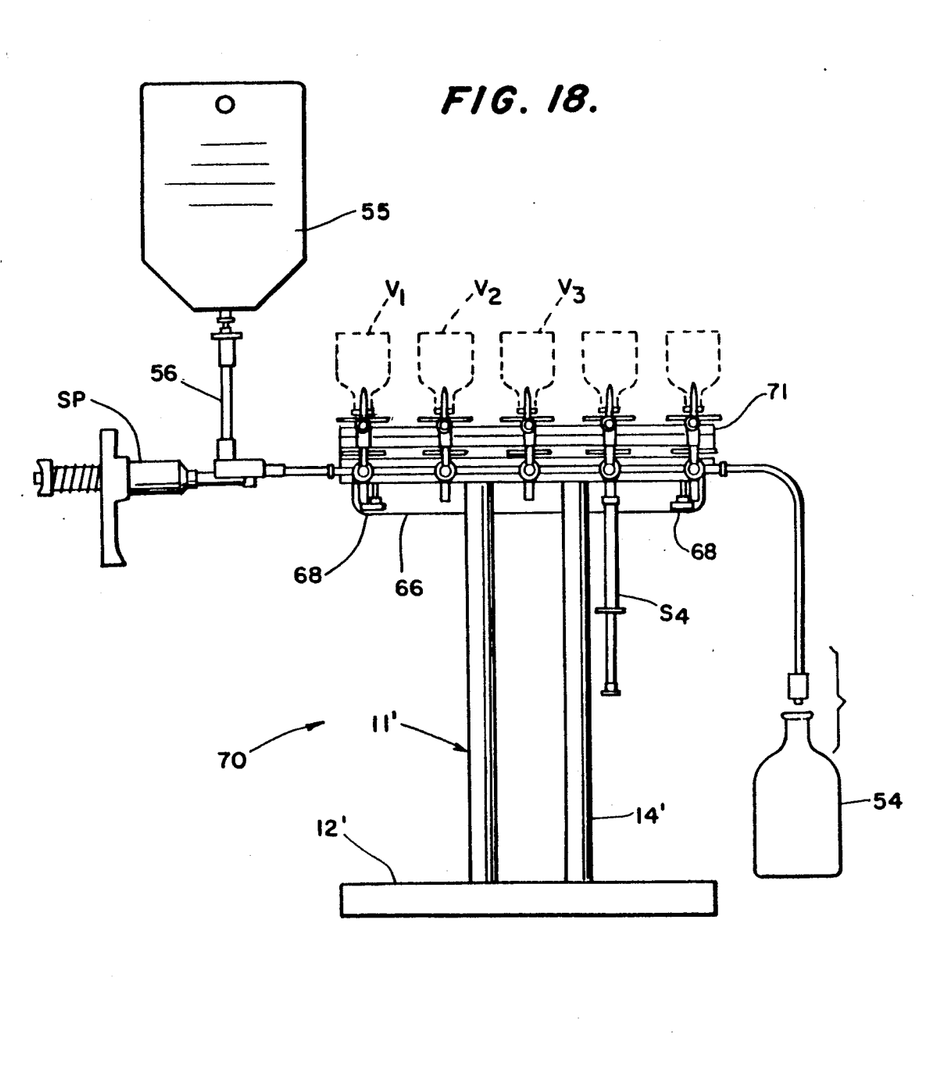
FIG. 18 is a view in elevation of a further modified apparatus for mixing parenteral nutrition solutions, in which a different stand and valving means are used.
Figure 19:
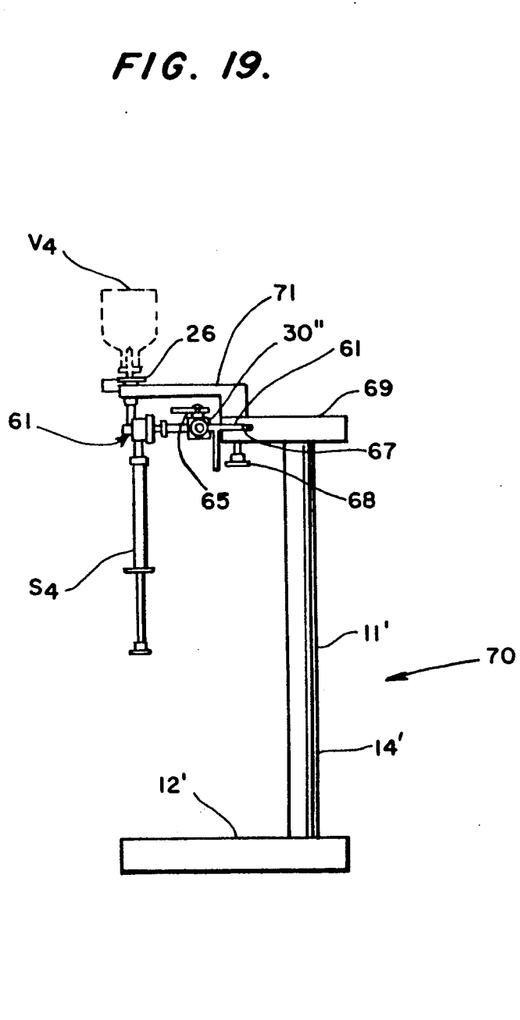
FIG. 19 is an end view of the apparatus of FIG. 18.

A second modification of the invention is represented generally at 70 in FIGS. 18 and 19. In this form of the invention, a multi-way valve 61 and vented spike 26 of the type shown in FIGS. 15 through 17 are used. However, the multi-way valve 61 is connected to a modified manifold 30" through a valved connection 65, and the manifold 30" is carried on one arm of a T-shaped bracket 66 which has its other arm releasably fixed in a slot 67 on a modified stand 11'. Set screws 68 extend through the rack 69 of the stand 11' into engagement with the arm of the fitting 66 to retain it in the slot 67. The bracket 69 is permanently affixed to the upper ends of arms 13' and 14' which are, in turn, secured at their lower ends to a base 12'. The vented spike 26 and vials $V_1$, $V_2$, etc. are carried on the end of an L-shaped bracket 71 extending forwardly from a top edge portion of the bracket 69. In all other respects this form of the invention is substantially as previously shown and described, and functions substantially identical, to the form of the invention in FIGS. 1 and 2.

Figure 20:
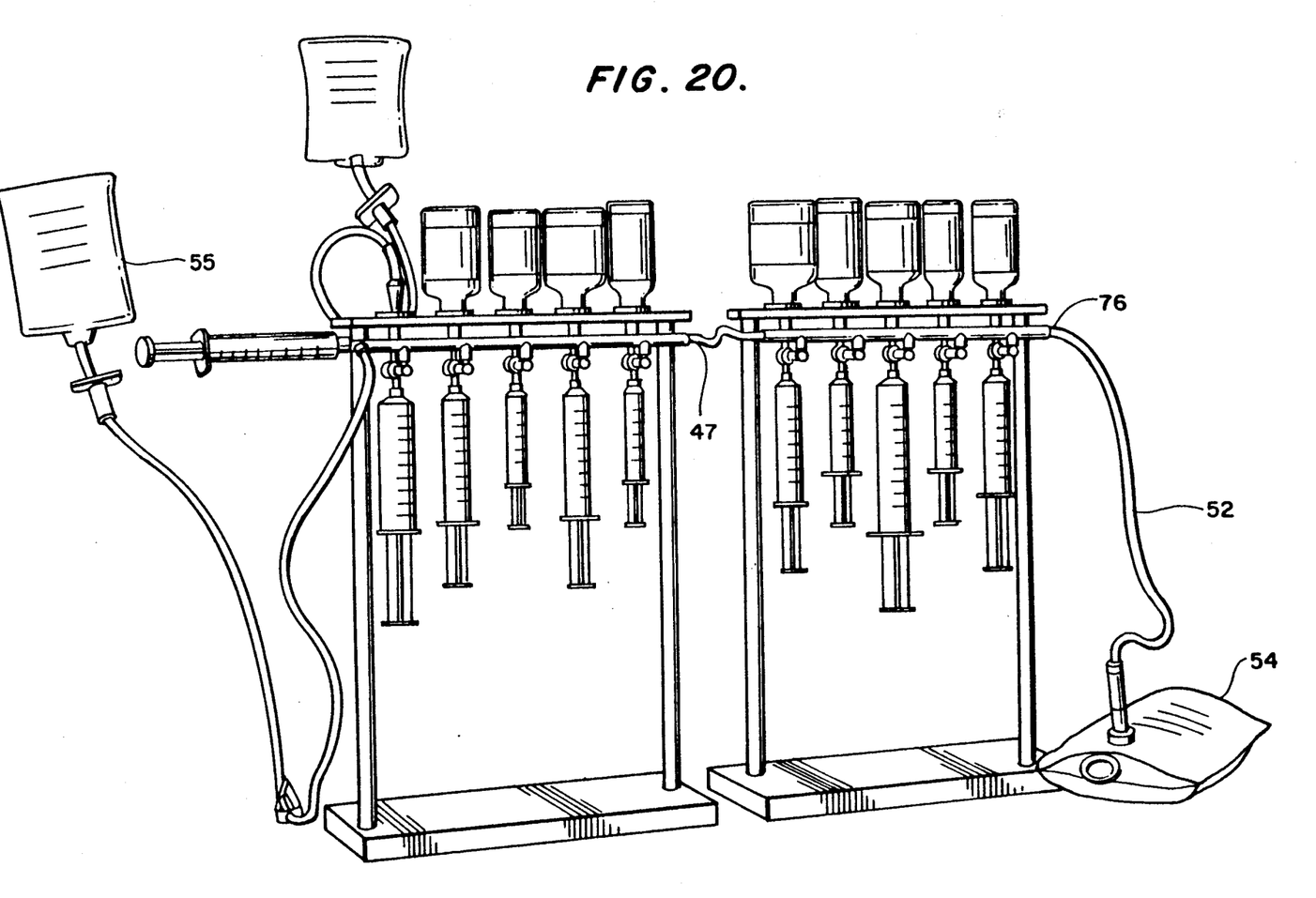
FIG. 20 is a perspective view of an apparatus according to FIG. 1, in which two stands and sets of vials are connected in tandem.

In FIG. 20, a further variation of the invention is represented generally at 80, wherein a plurality of the assemblies shown in FIGS. 1 and 2 are connected in tandem for admixing even further additives in producing a parenteral nutrition solution. In this arrangement, a length of tubing 81 connects the outlet end of a first manifold 47 with the inlet end of a second manifold 82, and the outlet of the second manifold is connected through a length of tubing 52 with the final solution container 54.

The apparatus of the invention provides a fast and efficient method for producing a total parenteral nutrition solution and assures sterile preparation of the final mixture due to the elimination of all vial and needle manipulations. Further, the risk of medication dosage error is substantially reduced since the vial and dedicated syringe is always held in aligned relationship for ready visual identification of the additive being selected and the level of that additive. Moreover, the apparatus of the invention places the vials, manifold and syringes in the most effective physical position for sterile laminar airflow under the hood of the sterile environment containment device. The apparatus of the invention is also compact in design, saving valuable space for other uses. The combination of multi-way valves and couplings to the manifold are designed such that minimum dead space is created, thus resulting in a minimum amount of residual fluid following a transfer operation. In addition, the flushing assembly attached to the manifold permits any residual fluid which does remain to be flushed into the final container following a transfer operation. Still further, the completely closed system approach to the compounding of the numerous additives and their transfer to the final mixture container minimizes or eliminates any breaches in the sterile environment.

Although the invention has been described with reference to particular embodiments, it is to be understood that these embodiments are merely illustrative of the application of the principles of the invention. Numerous modifications may be made therein and other arrangements may be devised without departing from the spirit and scope of the invention.

We claim:

1. An apparatus for preparing parenteral nutrition solutions from a plurality of additives contained in individual vials having sealed ends, comprising:
   a rack for supporting the vials in a predetermined relationship adjacent one another, said rack having means thereon for contacting and supporting said vials in said predetermined relationship, and having quick release means for releasable attachment of said rack on a stand, said rack further having openings therethrough aligned with the positions of said vials on said rack means;
   means for piercing the sealed ends of said vials to gain access to the contents thereof, through a respective opening in the rack means and into the sealed end of an associated vial, the piercing means being held on one side of the rack and an associated vial being held on the other side, said piercing means including means for attachment thereto of a pump for withdrawing additive from the associated vial, wherein an individual pump is held in associated, aligned relationship with each vial, whereby a plurality of vials and associated piercing means may be assembled to said rack and the assembly of the rack, the vials and the piercing means releasably atached to a stand, wherein:
   said rack comprises an elongate, rectangularly shaped, flat bar, said openings being spaced along the length of the bar, said means for contacting and supporting the vials comprises upstanding cylindrical walls on a top surface of the bar, and said quick release means comprises key-hole shaped openings through the opposite ends of the bar; and
   said stand includes a pair of elongate arms projecting in a common direction from a base, said arms having headed ends for engagement in said key-hole shaped openings and being flexible to align the headed ends with the larger part of the key-hole shaped openings whereby the headed ends may be passed through the key-hole shaped openings to enable the bar to be attached to and removed from the arms.

2. An apparatus as claimed in claim 1, wherein:
   the containers of additives comprise vials each having a stoppered end;
   said means for accessing the contents of the containers includes a piercing spike having a piercing end for penetrating the stoppered end;
   said pump means each comprises a syringe attached to a respective piercing spike;
   a manifold means is connected with the syringes to receive the additives from the syringes attached to the respective vials;
   a multi-way valve means is connected with each syringe to control flow from the associated vial, to the syringe and thence into the manifold;
   said multi-way valve means comprises a valve body having a first one-way valve to enable flow from a vial into the associated syringe but prevent reverse flow from the syringe into the vial, and a second one-way valve to enable flow from the syringe into the manifold but prevent reverse flow from the manifold to the syringe, said one-way valves being constructed and positioned relative to the manifold so as to minimize residual material in the apparatus; and
   a flushing means is connected with the manifold means to flush any residual material from the manifold means following transfer of an additive from its container to the final solution container.

3. A method of mixing a plurality of additives to produce a parenteral nutrition solution, comprising the steps of:
   supporting a plurality of vials containing the additives in predetermined relationship to one another;
   attaching a plurality of pump means in predetermined aligned relationship with the vials so that a pump means is provided for each vial and is held in aligned relationship thereto;
   using the pump means to successively draw the additives from the vials and expel the additives into and through a manifold to a container for the parenteral nutrition solution; and
   flushing the manifold with a flushing solution to remove any residual additives from the manifold following a mixing procedure.

4. A method as claimed in claim 3, including the steps of:
   supporting the vials and pump means on a disposable rack; and
   releasably attaching the rack to a stand, said vials and pump means being assembled to the rack after to attachment of the rack to the stand.

* * * * *